United States Patent
Gul

(10) Patent No.: US 6,628,396 B1
(45) Date of Patent: Sep. 30, 2003

(54) PHOTO EXPANSION GAS DETECTOR

(75) Inventor: S. Asim Gul, Orono, MN (US)

(73) Assignee: Mamac Systems, Inc., Eden Prairie, MN (US)

(*) Notice: Subject to any disclaimer, the term of this patent is extended or adjusted under 35 U.S.C. 154(b) by 213 days.

(21) Appl. No.: 09/591,755

(22) Filed: Jun. 12, 2000

Related U.S. Application Data

(60) Provisional application No. 60/139,062, filed on Jun. 11, 1999.

(51) Int. Cl.[7] .................. G01N 21/00; G01N 15/06; G01J 5/02
(52) U.S. Cl. .................. 356/437; 250/343; 250/573
(58) Field of Search .................. 356/432, 437, 356/440; 250/222.2, 573, 574, 576, 343–344

(56) References Cited

U.S. PATENT DOCUMENTS

| 3,787,694 A | * | 1/1974 | Owen ..................... 250/338.1 |
| 4,019,056 A | | 4/1977 | Block et al. ............... 250/344 |
| 4,051,372 A | | 9/1977 | Aine ........................ 250/343 |
| 4,055,764 A | * | 10/1977 | Dimeff ..................... 250/336.1 |
| 4,094,608 A | | 6/1978 | Young ...................... 356/97 |
| 4,197,752 A | | 4/1980 | Block ....................... 73/755 |
| 4,236,827 A | | 12/1980 | Horiba et al. .............. 356/437 |
| 4,293,316 A | | 10/1981 | Block ....................... 55/16 |
| 4,355,234 A | * | 10/1982 | Fertig et al. ............... 250/343 |
| 4,360,955 A | | 11/1982 | Block ....................... 29/25.42 |
| 4,740,086 A | | 4/1988 | Oehler et al. .............. 356/432 |
| 4,886,681 A | | 12/1989 | Clabes et al. .............. 427/38 |
| 4,903,248 A | | 2/1990 | Fertig ....................... 367/140 |
| 4,996,627 A | * | 2/1991 | Zias et al. ................. 361/283.4 |
| 5,125,749 A | | 6/1992 | Leugers et al. ............. 356/432 |
| 5,589,689 A | * | 12/1996 | Koskinen .................. 250/339.01 |
| 5,677,534 A | * | 10/1997 | Araya ....................... 250/345 |
| 6,006,585 A | | 12/1999 | Forster ..................... 73/24.01 |

* cited by examiner

Primary Examiner—Loha Ben
Assistant Examiner—William Choi
(74) Attorney, Agent, or Firm—Kinney & Lange, P.A.

(57) ABSTRACT

A photo expansion gas detector includes a radiation emitter, a sample gas, an expansion gas hermetically sealed in a chamber, and a capacitive diaphragm for sensing pressure changes. The radiation emitter may be constant or may be cycled on and off. Radiation passes through the sample and into the expansion gas. The expansion gas expands according to the intensity of the radiation received. The capacitive diaphragm is impacted directly by the expansion gas. The capacitive diaphragm deflects relative to a fixed capacitive plate, resulting in changes in capacitance representing expansion and contraction of the expansion gas. The electrical signal generated by the changes in capacitance represent changes in the gas composition of the sample. The electrical signals are then processed to activate control systems.

29 Claims, 3 Drawing Sheets

PHOTO EXPANSION GAS DETECTOR

CROSS-REFERENCE TO RELATED APPLICATION(S)

This application claims priority from provisional application No. 60/139,062 filed Jun. 11, 1999.

BACKGROUND OF THE INVENTION

The present invention relates to detection of gases, and, more particularly, to the detection of changes in the compositional amounts of gases in air or in a gaseous exhaust product.

Gas detection is important in numerous contexts. For instance, smoke and fire alarms may detect the presence of any of various gases or particles in the air. Carbon dioxide is an example of one of such gases. Carbon dioxide is given off as a bi-product of combustion reactions. Carbon dioxide concentrations in air significantly increase if combustion is occurring in a closed space or nearby. The carbon dioxide given off disperse through the air, and the dispersion may occur more rapidly and in different directions (such a radially outward rather than rising with heat) than smoke or water vapor dispersion. Depending somewhat upon the material and conditions of combustion, smouldering combustion may produced a significant amount of carbon dioxide prior to significant production of smoke and prior to bursting into flames. Accordingly, detecting a rapid increase in the carbon dioxide concentration in the air may signal an alarm condition earlier than possible with conventional smoke detectors.

Gas detection is also significant in other venues. Detection of natural gas or other fuel gases may be important to assure that the natural gas or fuel gas is maintained within the pipe lines without leakage. Carbon monoxide detection is important for health and safety concerns of human breathing. Auto emissions may use gas detectors to verify adequate combustion of the fuel, to minimize hydrocarbons and/or carbon monoxide in resulting exhaust.

Photoacoustic gas detection is known in the art as described for example in U.S. Pat. Nos. 6,006,585, 5,125, 749, 4,903,248, 4,886,681, 4,740,086 and 4,236,827, and patents discussed in the background of U.S. Pat. No. 4,094, 608. As early as 1880, Alexander Graham Bell reported the acoustic effect induced by thin discs to interrupted beams of light. Photoacoustic gas detection devices use interrupted radiation of a preselected wave length to irradiate or pass through the gas to be measured. Regular modulation of the radiation intensity creates sound waves that can be detected with a very sensitive microphone.

Due to the required sensitivity of the microphone, the molecular sample and the microphones must be heavily insulated to limit uncertainty in the photo acoustic reading due to external acoustic vibrations. While the microphone technology has become increasingly sophisticated, leading to improvements in the sensitivity of the photo acoustic gas detectors, the sensitivity of the gas detector is limited by the sensitivity of the microphones and by the ability to insulate against external acoustic vibrations. In addition, while interference of varying frequencies may be eliminated through various calculations, interference of the same frequency as the acoustic waves formed by the excited molecules in the sample cannot be systematically eliminated by calculation without jeopardizing the accuracy of the reading. Interference at the same frequency as the excited molecular sample would be indistinguishable from the acoustic wave to be measured.

Photoacoustic gas detectors may be fairly expensive, particularly depending upon the required accuracy of the microphone. A highly accurate photoacoustic gas detector would require a great deal of sound insulation to prevent ambient interference. The requirement that the radiation be modulated at an acoustic frequency which can be sensed by the microphone also adds costs. U.S. Pat. No. 4,094,608 shows one alternative, but requires the sample to be absorbed or dissolved or embedded into a layer of electrical insulating material. Thus the sample must be collected prior to spectroanalysis, and the collection procedure must be separately performed. A low cost, accurate, and highly sensitive gas detector, which does not require complicated sample collection, would find a wealth of uses.

BRIEF SUMMARY OF THE INVENTION

The present invention is a photo expansion gas detector, which detects the gas content of its environs by capacitively sensing a changes in position of a diaphragm moved by expansion and/or contraction of a known gas in a sealed container. The photo expansion gas detector, includes a radiation emitter which directs radiation through a sample gas and into an expansion gas chamber. A diaphragm is in contact with the expansion gas and moves when the expansion gas expands or contracts. The capacitive diaphragm deflects relative to a fixed capacitive plate, resulting in changes in capacitance representing expansion and contraction of the expansion gas. The electrical signal generated by the changes in capacitance represents changes in the gas composition of the sample.

While the above-identified drawing figures set forth a preferred embodiment, other embodiments of the present invention are also contemplated, some of which are noted in the discussion. In all cases, this disclosure presents the illustrated embodiments of the present invention by way of representation and not limitation. Numerous other minor modifications and embodiments can be devised by those skilled in the art which fall within the scope and spirit of the principles of this invention.

DETAILED DESCRIPTION

Figure 1:
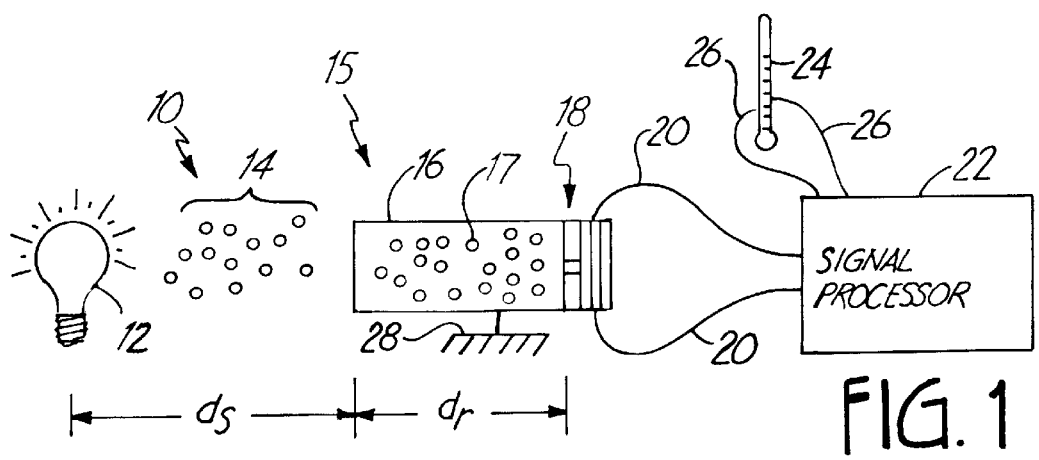
FIG. 1 is a schematic view of a gas detector of the present invention.

FIG. 1 shows a photo expansion gas detector 10 according to the present invention. The gas detector 10 includes an electromagnetic radiation source or emitter 12, schematically shown as a light bulb. Emitter 12 shines electromagnetic radiation through a gas sample 14. The radiation, after passing through gas sample 14, is received in an expansion receiver 15.

The expansion receiver 15 includes a chamber 16 hermetically sealed around a receiver gas 17. The front wall of the chamber 16 is transparent to the radiation, at least within a critical frequency band of interest, such that the receiver gas receives substantially all of the radiation passed through sample 14 within the desired frequency band.

A capacitive diaphragm 18 is coupled to the chamber 16 and in communication with the receiver gas 17. Expansion of the receiver gas 17 causes movement of the diaphragm 18. A movable capacitor plate is provided on the diaphragm 18. For instance, the diaphragm may be formed of a semiconductor such that the diaphragm itself form the movable capacitor plate. Alternatively, a conductive plate may be deposited on a face of a diaphragm formed of a different material. A fixed capacitive plate 19, generally parallel to the movable capacitor plate of the diaphragm 18, is spaced a small gap from the diaphragm 18. Upon movement of the diaphragm 18, the moving capacitor plate changes its position relative to the fixed capacitive plate 19, which changes the capacitive response between the fixed capacitive plate 19 and the capacitive diaphragm 18. Electrical leads 20 complete an electrical circuit so the capacitive response of the diaphragm 18 can be interpreted by a signal processor 22. A temperature sensor 24 (schematically shown as a thermometer) provides a temperature compensation value through leads 26 to the signal processor 22.

The type of radiation emitter 12 is selected based upon the desired gas to be detected. As known in the art of spectrometry, each gas has a characteristic signature of absorbed/reflected/transmitted radiation frequencies. The emitter 12 must emit radiation at the characteristic frequencies of the gas to be detected. For example, carbon dioxide has a characteristic frequency of radiation having a wavelength of around 4 microns. If carbon dioxide concentrations are to be detected, the emitter 12 should emit a substantial amount of radiation in the four micron wavelength band.

The amount of the characteristic frequency radiation (4 micron) transmitted through the sample 14 depends upon the test gas (carbon dioxide) content of the sample. The larger the test gas (carbon dioxide) content, the less characteristic frequency (4 micron) radiation will be transmitted to the expansion receiver 15.

The receiver gas 17 sealed within the expansion receiver 15 has a known composition. For example, the receiver gas 17 for detecting the carbon dioxide concentration in sample 14 may be substantially pure or 100% carbon dioxide. Alternatively, the receiver gas 17 may be a different gas having a significant concentration of carbon dioxide. The significant property of the receiver gas 17 is that it receives the radiation passed through the sample 14 and expands based on the excitement of its molecules. For example, 4 micron wavelength radiation excites carbon dioxide molecules.

The intensity of the 4 micron wavelength radiation after passing through the sample 14 determines the energy state of the receiver gas 17. The lower the test gas concentration in the sample 14, the more characteristic frequency is transmitted through the sample 14, the more characteristic frequency is received by the receiver gas 17, the more the receiver gas 17 expands.

The preferred emitter emits a narrow frequency band of the characteristic wavelength for the test gas to be detected. However, cost considerations may require the selection of an emitter of a wider frequency band. For instance, one preferred emitter is an incandescent lamp with a Tungsten filament. An infrared light bulb or a light emitting diode may alternatively be used, or other types of radiation emitters. The significant factor is that the intensity of transmission through the sample 14 depends upon the concentration of the test gas, and that excitement of the expansion gas 17 depends upon the intensity of radiation transmitted through the sample 14.

The intensity of characteristic radiation transmitted through the sample 14 is dependent upon the distance $D_s$, that the wavelength radiation travels through the sample 14. At the same time, the amount of radiation energy absorbed in the receiver gas 17 is dependent upon a distance $D_r$ which is characteristic of the chamber 16. The geometry of the chamber 16 may be selected to maximize the amount of radiation received through the sample 14 and to provide the maximum amount of expansion of receiver gas 17 upon capacitive diaphragm 18 per radiation received. Preferably, the distance $D_r$ is enough that the receiver gas 17 is substantially opaque to the signature wavelength radiation at the intensity admitted by the emitter 12. In a preferred embodiment, the distance $D_s$ is about 2 inches and the distance $D_r$ is about ½ inch.

The capacitive diaphram 18 may be for instance a thin film silicon capacitive diaphragm having a known dielectric gap in a baseline position. An example of one such silicon substrate capacitive diaphragm is provided in U.S. Pat. No. 4,996,627, which is incorporated herein by reference. FIGS, 6 and 7 generally depict the structure disclosed in U.S. Pat. No. 4,996,626, including a diaphragm 18 disposed between two fixed capacitive plates 19. Hole 21 allows the diaphragm 18 to be impacted by pressure on a first side. If desired, hole 23 allows diaphragm 18 to be impacted by pressure on an opposing side. When the receiver gas 17 expands, it pushes on the diaphragm 18, resulting in a change in capacitance across the dielectric gap. Because of the change in capacitance, the electrical signal across leads 20 can "see" the amount of expansion and the amount of movement of the capacitive diaphragm 18. Signal processor 22 analyzes the signal across leads 20 to precisely determine movement of the capacitive diaphragm 18, and accordingly the expansion or excitement state of the receiver gas 17.

In a sense, the expansion receiver 15 can be thought of as a test tube with a balloon attached on top of it. When air in the test tube is heated to a higher molecular excitement state, the air expands and blows up the balloon. In the context of the present invention, the capacitive diaphragm 18 is similar to the balloon in that the thin silicon diaphragm moves based on excitement/expansion of the receiver gas 17. The capacitive signal across the known di-electric gap in the expansion receiver 15 produces an electrical signal which is similar to viewing the blowing up of the balloon.

As noted in the above "test tube/balloon" analogy, temperature changes also cause expansion of the receiver gas 17. Accordingly, a temperature sensor 24 measures ambient conditions to compensate for the temperature of receiver gas 17 on the capacitive responsive of diaphragm 18.

The expansion receiver 16 may be supported on or within an insulated support 28 so that the diaphragm 18 is not moved or effected by other conditions which do not need sensing. For instance, depending upon the period 36 of the emissions/receiver gas expansion, the chamber 16 may need to be insulated from sound. The chamber 16 may also need to be insulated from electromagnetic radiation, such as sealed from ambient light or from sunlight. The support 28 may also need to thermally insulate the chamber 16, or to insulate the chamber 16 from vibration depending upon the environment of use. For example, use of the gas detector 10 in an automotive exhaust may need one or all of thermal, vibration, acoustic or light insulation.

Figure 2:
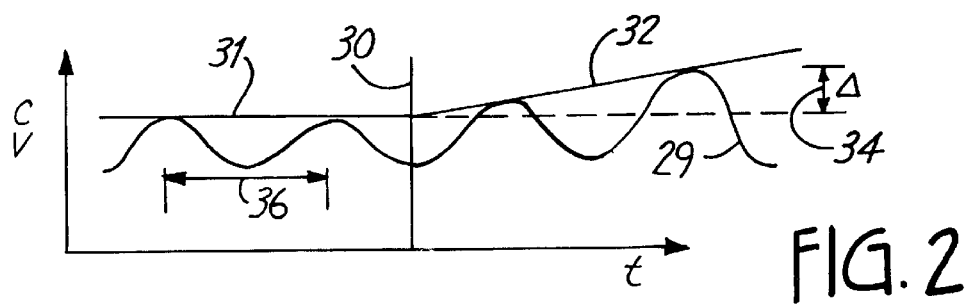
FIG. 2 is a representation of a signal generated with the gas detector of FIG. 1 across an alarm condition.

FIG. 2 indicates a capacitive signal received by processed in the signal processor 22. Depending upon how the signal is processed, the electrical signal 29 may be indicative of capacitance, of the position of the silicon diaphragm relative to the known di-electric gap, or of the excitement/expansion state of the receiver gas 17.

In a preferred signal shown in FIG. 2, the emitter 12 and the electromagnetic radiation is oscillated, generally producing the sine wave signal 29 shown. Alternatively, the radiation may be oscillated in waves other than a sine wave, or may not be oscillated at all.

At time 30 an event occurs which causes the test gas concentration in the sample 14 to increase. For instance, the event 30 might be the beginning of combustion within a room. Prior to event 30, the peaks of the signal 29 produce a relatively flat base line 31. After event 30, such as the concentration of carbon dioxide in the room increases, the peaks of the signal 29 produce a sloped increase 32 The signal 29 can be processed both to determine the slope of the increasing portion 32 and to determine the overall change in test gas concentration 34. Both the slope 32 and the change 34 may indicate whether corrective action may be taken.

For instance, after relatively minute combustion begins, the carbon dioxide concentration in a room may increase to 2–10 times the normal carbon dioxide concentration in the air, such as an increase from 500 parts per million to approximately 10,000 parts per million. If a carbon dioxide concentration increases more than 1,000 parts per million within a predetermined time period of several minutes, an alarm condition may sound. The alarm alerts the fact that combustion is occurring in the room, even before there is a substantial amount of smoke produced, and before flame ignites.

If desired for the resultant signal output, the radiation emitter 12 may be oscillated, resulting in a signal 29 of period 36. For instance, the emitter 12 may be cycled at an audible frequency of 15 hertz to 20 kilohertz, or more preferably at 2–10 kilohertz. However, the emitter 12 may also be held in constant state or be period 36 may be substantially longer. For instance, it may be important to take sample values at least once per second or once per minute, and the period 36 may be longer than the audible range, such as a period of one second or one minute. Period 36 should be selected based upon a consideration of maximizing the amount of expansion for a given amount of radiation, ease of signal processing, degradation of the detector 10, and how quickly changes in the sample 14 need to be identified in the particular environment. In a preferred embodiment, the emitter 12 is oscillated at a frequency of less than 15 cycles per second. The slower oscillation—at an inaudible frequency which is generally not considered an "acoustic" wave—produces a greater magnitude of expansion in the expansion gas so as to be more reliably sensed.

With using a lamp as the emitter 12, the filament of the lamp may degrade over time, particularly if the lamp is oscillated or cycled. Problems due to degradation on the filament due to cycling may be minimized in at least two different ways.

Figure 3:
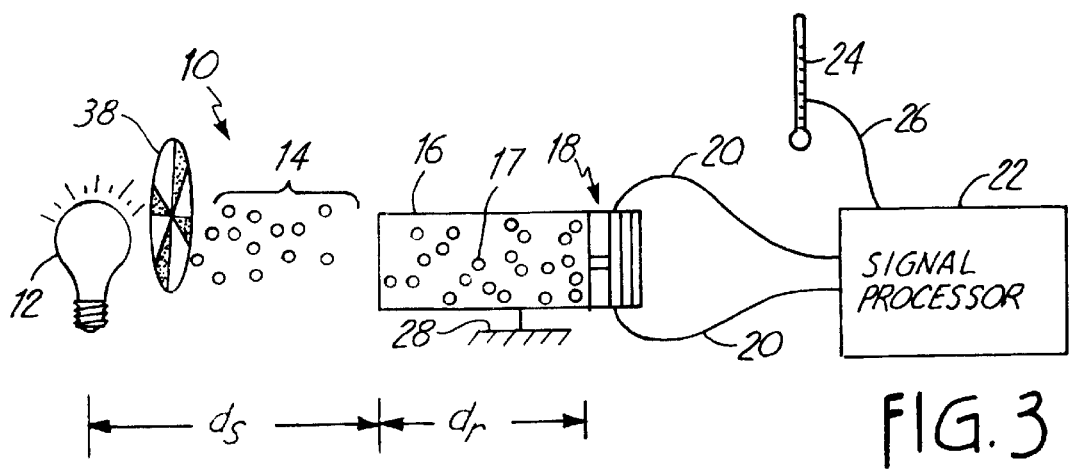
FIG. 3 is a schematic view of an alternative gas detector of the present invention.

As shown in FIG. 3 a radiation interrupter 38 may be interposed, such as between the emitter 12 and the sample 14. The radiation interrupted will thus cause an alternating on and off for the critical wavelength emission transmitted through the sample 14 and into the expansion receiver 15. A simple form of radiation interrupter 38 is a disk which has openings therethrough but rotates.

Figure 4:
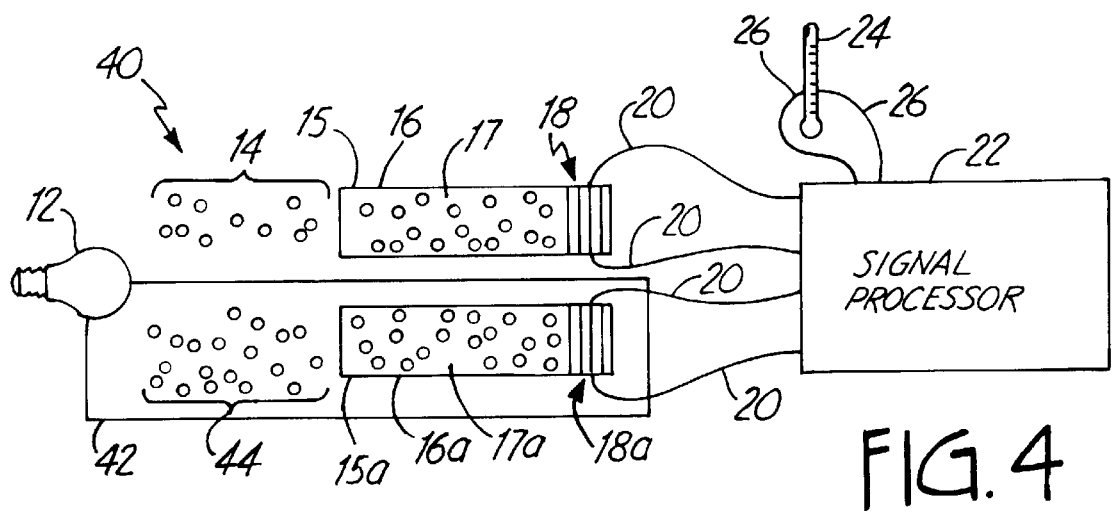
FIG. 4 is a schematic view of another alternative gas detector of the present invention.

FIG. 4 shows an alternative gas detector 40 to minimize problems due to degradation of the emitter 12. Gas detector 40 can be used in substitution or in combination with the radiation interrupter 38 of FIG. 3. In gas detector 40, an alternative radiation path is provided through a sealed control chamber 42. The radiation thus travels on parallel paths through a control gas 44 as well as the sample gas 14. For example, the control gas 44 may be nitrogen which is effectively transparent to the 4 micron wavelength. Alternatively, the control gas 44 may be air or another gas having a desired concentration of the test gas.

While the control chamber 42 is hermetically sealed, it is preferably not formed entirely of rigid materials, but rather has at least one flexible wall permitting its volume to change. By adequate design of the control chamber, the pressure of the control gas 44 can mirror the pressure of the sample 14, such that barometric and altitude changes do not affect the relative test gas concentration between sample 14 and control gas 44.

Radiation through the control gas 44 is received in a second expansion receiver 15a. If desired, the controlled expansion receiver may include a different receiver gas 17a. In the preferred gas detector 40, the gas in both expansion receivers 15, 15a is identical. In the gas detector 40, the expansion sensed by capacitive diaphragm 18 can be compared against the expansion sensed by capacitive diaphragm 18a. In this way, any change in signal resulting from degradation of emitter 12 can be determined.

Figure 5:
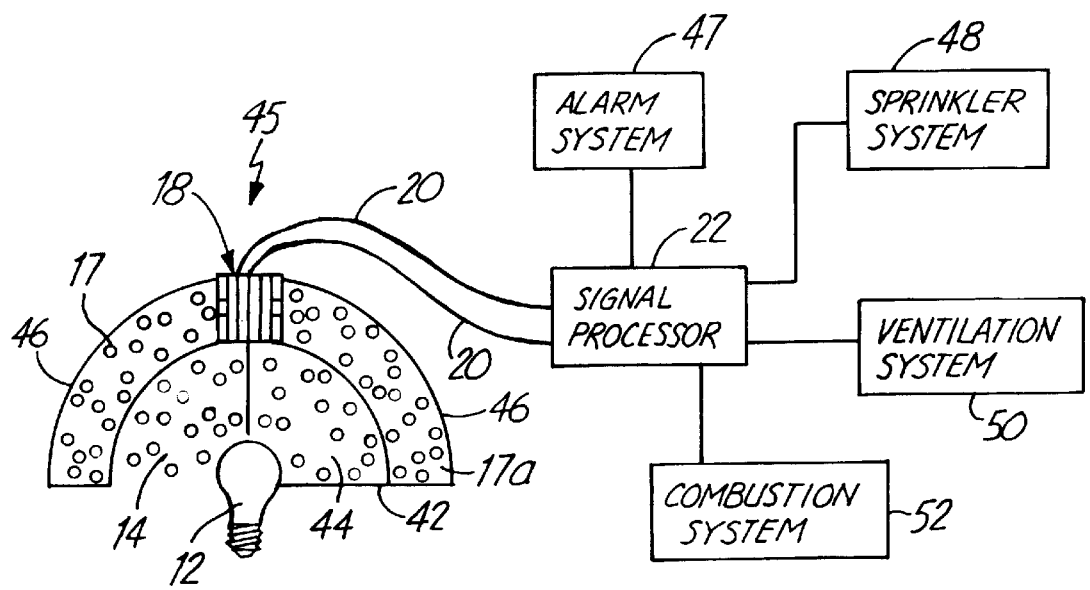
FIG. 5 is a schematic view of another alternative gas detector of the present invention.
Figure 6:
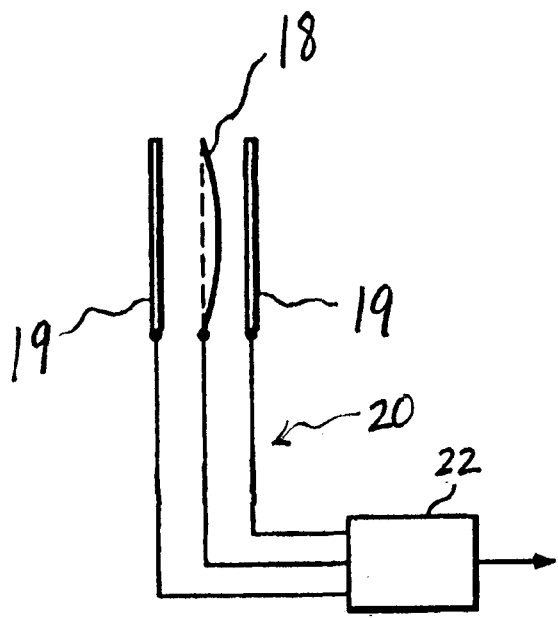
FIG. 6 is a simplified illustration of an example of a silicon substrate capacitive diaphragm useful with the present invention.
Figure 7:
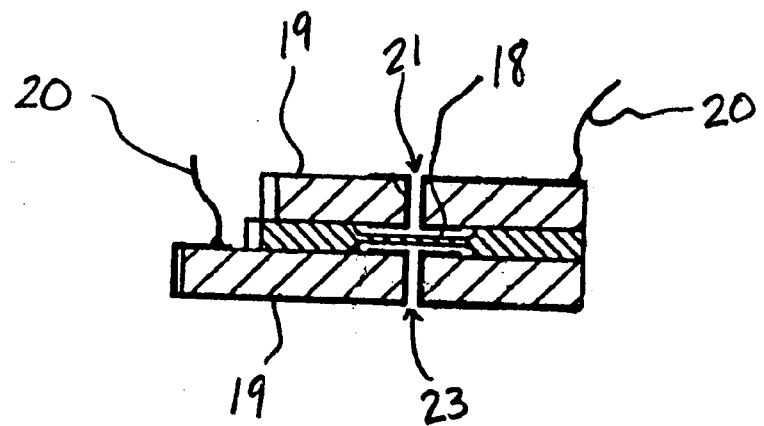
FIG. 7 is a cross-sectional view of a generalized tri-level transducer structure as an example of a silicon substrate capacitive diaphragm design useful with the present invention.

FIG. 5 shows an alternative gas detector 45. The gas detector 45 includes a chamber 46 which has an alternative configuration. A single capacitive diaphragm 18 is used between both the expansion chamber 46 for the receiver gas 17 and for the control receiver gas 17a. In the gas detector 45, the position of the single capacitive diaphragm 18 is strictly due to the relative expansion between receiver gas 17 and control receiver gas 17a. Accordingly, temperature expansion is automatically accounted for, and no separate temperature sensor 24 is required.

The chamber 46 can be geometrically oriented as desired for the maximum possible reception/absorption of the critical wavelength. The capacitive diaphragm need not be oriented transverse or perpendicular to the direction of radiation emission.

As shown in FIG. 5, the signal processor 22 can then be used to run various components. For instance, if the signal response indicates combustion, an alarm system 47 may sound, or a sprinkler system 48 may be activated. If the signal response indicates an increase in carbon dioxide content of an amount/timing merely due to an increased number of people within a room, a ventilation system 50 may be activated to eliminated a "stuffy feeling" within the room. Alternatively, the signal processor 22 may activate or control a combustion system 52, such as in a furnace of a home or in an internal combustion engine.

Although the present invention has been described with reference to preferred embodiments, workers skilled in the art will recognize that changes may be made in form and detail without departing from the spirit and scope of the invention.

What is claimed is:

1. A gas detector comprising:
   a radiation emitter;
   a first expansion receiver spaced from the radiation emitter by a sample distance, the first expansion receiver comprising:
      a chamber hermetically housing an expansion gas such that radiation from the radiation emitter is transmitted through a sample into the expansion gas, the expansion gas having a known composition which expands based upon intensity of radiation received; and a capacitive diaphragm sensor comprising:
  a movable capacitor plate area provided on a diaphragm which is impacted by the expansion gas; and
  a fixed capacitor plate, supported generally parallel the movable capacitor plate area and separated from the movable capacitor plate area by a dielectric gap which changes thickness when the diaphragm moves, the fixed capacitor plate and the movable capacitor plate area having a capacitance across the dielectric gap such that expansion of the expansion gas produces a corresponding change in capacitance;

a control chamber sealed with a known control gas therein which receives radiation from the radiation emitter; and a second expansion receiver housing a control expansion gas such that radiation from the radiation emitter is transmitted through the control chamber into the control expansion gas the control expansion gas being separated from the expansion gas such that the gas detector can sense changes in the expansion gas relative to the control expansion gas.

2. The gas detector of claim 1, wherein the dielectric gap contains expansion gas.

3. The gas detector of claim 1, wherein one side of the capacitive diaphragm is in fluid communication with the expansion gas and an opposing side of the capacitive diaphragm is in communication with a known pressure.

4. The gas detector of claim 1, further comprising:
a signal processor for detecting tested gas in the sample based upon an electrical signal across the capacitive diaphragm, wherein the signal processor detects a concentration of tested gas, a change in concentration of tested gas, or a rate of concentration change of tested gas.

5. The gas detector of claim 1, wherein tested gas in the sample has a characteristic radiation absorption frequency, and wherein the expansion gas is substantially opaque to radiation from the radiation emitter of the radiation absorption frequency.

6. The gas detector of claim 1, wherein the expansion gas is a substantially pure concentration of tested gas in the sample.

7. The gas detector of claim 1, further comprising insulation to shield the first expansion receiver and the second expansion receiver from heat, electromagnetic radiation, acoustic waves or vibrations.

8. The gas detector of claim 1, wherein the radiation emitter cycles.

9. The gas detector of claim 8, wherein the radiation emitter cycles less than 15 times per second.

10. The gas detector of claim 1, further comprising a radiation interrupter.

11. The gas detector of claim 1, wherein the radiation emitter is a lamp with a tungsten filament.

12. The gas detector of claim 1, wherein the capacitive diaphragm is a thin film silicon diaphragm, and the movable capacitor plate area is provided by the silicon.

13. The gas detector of claim 1, wherein the control chamber has a variable volume to normalize the control gas to ambient pressure of the sample.

14. The gas detector of claim 1, wherein the second expansion receiver comprises a second capacitive diaphragm.

15. The gas detector of claim 1, wherein the radiation emitter has a single filament, wherein the first expansion receiver and the second expansion receiver each comprise a radiation entry surface which transmits radiation emitted from the single filament of the radiation emitter into the expansion receiver, and wherein the radiation entry surface of the first expansion receiver is not coplanar with the radiation entry surface of the second expansion receiver such that both the first expansion receiver and the second expansion receiver receive equivalent radiation from the single filament.

16. A gas detector comprising:
a radiation emitter;
a control chamber sealed with a known control gas therein which receives radiation from the radiation emitter; and
an expansion receiver spaced from the radiation emitter by a sample distance, the expansion receiver comprising:
  a chamber hermetically housing an expansion gas such that radiation from the radiation emitter is transmitted through a sample into the expansion gas, the expansion gas having a known composition which expands based upon intensity of radiation received; and
  a capacitive diaphragm which responds to expansion of the expansion gas with a change in capacitance across a dielectric gap, the capacitive diaphragm comprising:
    a movable capacitor plate area provided on a diaphragm which is impacted by the expansion gas; and
    a fixed capacitor plate, supported generally parallel the movable capacitor plate area and separated from the movable capacitor plate area by a dielectric gap which changes thickness when the diaphragm moves, the fixed capacitive plate and the movable capacitor plate area having a capacitance across the dielectric gap such that expansion of the expansion gas produces a corresponding change in capacitance,
  wherein the capacitive diaphragm is in communication with the expansion gas on one side and in communication with the control gas on an opposing side.

17. A gas detector comprising:
a radiation emitter;
a control chamber sealed with a known control gas therein which receives radiation from the radiation emitter, wherein the control chamber has a control gas pressure which varies to match ambient; and
an expansion receiver spaced from the radiation emitter by a sample distance, the expansion receiver comprising:
  a chamber hermetically housing an expansion gas such that radiation from the radiation emitter is transmitted through a sample into the expansion gas, the expansion gas having a known composition which expands based upon intensity of radiation received; and
  a capacitive diaphragm which responds to expansion of the expansion gas with a change in capacitance across a dielectric gap, the capacitive diaphragm comprising:
    a movable capacitor plate area provided on a diaphragm which is impacted by the expansion gas; and
    a fixed capacitor plate, supported generally parallel the movable capacitor plate area and separated from the movable capacitor plate area by a dielectric gap which changes thickness when the diaphragm moves, the fixed capacitive plate and the movable capacitor plate area having a capacitance across the dielectric gap such that expansion of the expansion gas produces a corresponding change in capacitance.

18. A gas detector comprising:
a radiation emitter;
a control chamber sealed;with a known control gas therein which receives radiation from the radiation emitter, wherein the control gas is nitrogen; and
an expansion receiver spaced from the radiation emitter by a sample distance, the expansion receiver comprising:
  a chamber hermetically housing an expansion gas such that radiation from the radiation emitter is transmitted through a sample into the expansion gas, the expansion gas having a known composition which expands based upon intensity of radiation received; and
  a capacitive diaphragm which responds to expansion of the expansion gas with a change in capacitance across a dielectric gap, the capacitive diaphragm comprising:
    a movable capacitor plate area provided on a diaphragm which is impacted by the expansion gas; and
    a fixed capacitor plate, supported generally parallel the movable capacitor plate area and separated from the movable capacitor plate area by a dielectric gap which changes thickness when the diaphragm moves, the fixed capacitive plate and the movable capacitor plate area having a capacitance across the dielectric gap such that expansion of the expansion gas produces a corresponding change in capacitance.

19. A gas detector comprising:
a radiation emitter;
a control chamber sealed with a known control gas therein which receives radiation from the radiation emitter, wherein the control gas is air; and
an expansion receiver spaced from the radiation emitter by a sample distance, the expansion receiver comprising:
  a chamber hermetically housing an expansion gas such that radiation from the radiation emitter is transmitted through a sample into the expansion gas, the expansion gas having a known composition which expands based upon intensity of radiation received; and
  a capacitive diaphragm which responds to expansion of the expansion gas with a change in capacitance across a dielectric gap, the capacitive diaphragm comprising:
    a movable capacitor plate area provided on a diaphragm which is impacted by the expansion gas; and
    a fixed capacitor plate, supported generally parallel the movable capacitor plate area and separated from the movable capacitor plate area by a dielectric gap which changes thickness when the diaphragm moves, the fixed capacitive plate and the movable capacitor plate area having a capacitance across the dielectric gap such that expansion of the expansion gas produces a corresponding change in capacitance.

20. A gas detector comprising:
a radiation emitter;
an expansion receiver spaced from the radiation emitter by a sample distance, the expansion receiver comprising:
  a chamber hermetically housing an expansion gas such that radiation from the radiation emitter is transmitted through a sample into the expansion gas, the expansion gas having a known composition which expands based upon intensity of radiation received; and
  a capacitive diaphragm which responds to expansion of the expansion gas with a change in capacitance across a dielectric gap, the capacitive diaphragm comprising:
    a movable capacitor plate area provided on a diaphragm which is impacted by the expansion gas; and
    a fixed capacitor plate, supported generally parallel the movable capacitor plate area and separated from the movable capacitor plate area by a dielectric gap which changes thickness when the diaphragm moves, the fixed capacitive plate and the movable capacitor plate area having a capacitance across the dielectric gap such that expansion of the expansion gas produces a corresponding change in capacitance;
  wherein the capacitive diaphragm is substantially planar and is disposed on a side of the chamber at a substantially non-perpendicular angle to radiation from the radiation emitter.

21. A gas detector comprising:
a radiation emitter;
an expansion receiver spaced from the radiation emitter by a sample distance, the expansion receiver comprising:
  a chamber hermetically housing an expansion gas such that radiation from the radiation emitter is transmitted through a sample into the expansion gas, the expansion gas having a known composition which expands based upon intensity of radiation received, wherein the chamber comprises a radiation entry surface which transmits radiation emitted from the radiation emitter into the chamber, wherein the radiation entry surface is non-planar; and
  a capacitive diaphragm which responds to expansion of the expansion gas with a change in capacitance across a dielectric gap, the capacitive diaphragm comprising:
    a movable capacitor plate area provided on a diaphragm which is impacted by the expansion gas; and
    a fixed capacitor plate, supported generally parallel the movable capacitor plate area and separated from the movable capacitor plate area by a dielectric gap which changes thickness when the diaphragm moves, the fixed capacitive plate and the movable capacitor plate area having a capacitance across the dielectric gap such that expansion of the expansion gas produces a corresponding change in capacitance.

22. An automatic response system, comprising:
a gas detector comprising:
  a radiation emitter;
  an expansion receiver spaced from the radiation emitter by a sample distance, the expansion receiver comprising:

a chamber hermetically housing an expansion gas such that radiation from the radiation emitter is transmitted through a sample into the expansion gas, the expansion gas having a known composition which expands based upon intensity of radiation received; and a capacitive diaphragm which responds to expansion of the expansion gas with a change in capacitance across a dielectric gap, the capacitive diaphragm comprising:

a movable capacitor plate area provided on a diaphragm which is impacted by the expansion gas; and a fixed capacitor plate, supported generally parallel the movable capacitor plate area and separated from the movable capacitor plate area by a dielectric gap which changes thickness when the diaphragm moves, the fixed capacitive plate and the movable capacitor plate area having a capacitance across the dielectric gap such that expansion of the expansion gas produces a corresponding change in capacitance;

a controlled system selected from the group consisting of alarm systems, sprinkler systems, ventilation systems, and combustion systems; and a processor for detecting tested gas in the sample based upon an electrical signal across the capacitive diaphragm, wherein the processor detects a concentration of tested gas, a change in concentration of tested gas, or a rate of concentration change of tested gas, compares the detected value against a stored threshold value, and automatically modifies the controlled system to take corrective action in events where the detected value passes the stored threshold value.

23. The automatic response system of claim 22, further comprising:

a temperature sensor for compensating expansion of the expansion gas due to temperature.

24. The automatic response system of claim 22, further comprising a control chamber sealed with a known control gas therein which receives radiation from the radiation emitter.

25. A method of detecting tested gas with a sample and controlling a controlled system based upon the detected value, comprising:

emitting radiation through a sample and into an expansion receiver, the expansion receiver comprising;

a chamber hermetically housing an expansion gas such that emitted radiation is transmitted through a sample into the expansion gas, the expansion gas having a known composition which expands based upon intensity of radiation received; and a capacitive diaphragm which responds to expansion of the expansion gas with a change in capacitance across a dielectric gap; and monitoring an electrical signal across the capacitive diaphragm so as assess a value of concentration of tested gas, a change in concentration of tested gas, or a rate of concentration change of tested gas;

comparing the assessed value against a stored threshold value; and automatically modifying a controlled system to take corrective action in events where the detected value passes the stored threshold value, the automatically modifying the controlled system being selected from the group consisting of sounding an alarm in an alarm system, activating a sprinkler system, activating a ventilation system, and activating or controlling a combustion system.

26. The method of claim 25, further comprising:

compensating for pressure through the use of:

a control chamber sealed with a known control gas therein which receives radiation from the radiation emitter, the control chamber having a variable volume to normalize to ambient pressure; and a second expansion receiver housing a control expansion gas such that radiation from the radiation emitter is transmitted through the control chamber into the control expansion gas, the control expansion gas being separated from the expansion gas.

27. The method of claim 25, further comprising:

compensating for temperature through the use of:

a control chamber sealed -with a known control gas therein which receives radiation from the radiation emitter; and a second expansion receiver housing a control expansion gas such that radiation from the radiation emitter is transmitted through the control chamber into the control expansion gas, the control expansion gas being separated from the expansion gas.

28. The method of claim 25, wherein the radiation emitter includes a single filament, and further comprising:

compensating for degradation of the emitted radiation from the single filament through the use of:

a control chamber sealed with a known control gas therein which receives radiation from the single filament of the radiation emitter; and a second expansion receiver housing a control expansion gas such that radiation from the radiation emitter is transmitted through the control chamber into the control expansion gas, the control expansion gas being separated from the expansion gas.

29. The method of claim 25, further comprising:

cycling the emitted radiation.

* * * * *